United States Patent [19]

Fleck et al.

[11] 4,167,629

[45] Sep. 11, 1979

[54] TRIAZOLYLSTYRENE COMPOUNDS

[75] Inventors: Fritz Fleck, Bottmingen; Horst Schmid, Münchenstein, both of Switzerland

[73] Assignee: Sandoz Ltd., Basel, Switzerland

[21] Appl. No.: 521,642

[22] Filed: Nov. 7, 1974

Related U.S. Application Data

[63] Continuation of Ser. No. 306,146, Nov. 13, 1972, abandoned.

[30] Foreign Application Priority Data

Nov. 19, 1971 [CH] Switzerland .................. 16866/71

[51] Int. Cl.$^2$ .................. C07D 403/10; C09B 23/14
[52] U.S. Cl. .................. 542/456; 260/157; 548/113; 542/419; 252/301.22; 548/257; 548/260; 548/261

[58] Field of Search .................. 260/240.9, 240 D; 542/456

[56] References Cited

U.S. PATENT DOCUMENTS 3,637,673  1/1972  Okubo et al. .................. 260/240.9

FOREIGN PATENT DOCUMENTS 751417 11/1970 Belgium .................. 260/240.9
1273478 5/1972 United Kingdom .................. 260/240.9

*Primary Examiner*—John D. Randolph
*Attorney, Agent, or Firm*—Gerald D. Sharkin; Richard E. Vila; Thomas C. Doyle

[57] ABSTRACT

This invention relates to new di-triazolylstyrene derivatives, useful as optical brighteners for organic polymeric materials, especially when applied to or incorporated in synthetic fibres.

1 Claim, No Drawings

TRIAZOLYLSTYRENE COMPOUNDS

This is a continuation of application Ser. No. 306,146, filed Nov. 13, 1972, now abandoned.

The present invention relates to triazolylstyrene compounds.

The invention provides compounds of formula I,

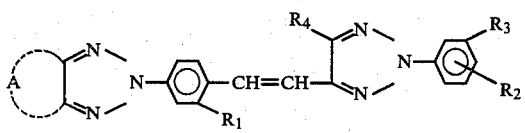

in which
R$_1$ signifies a hydrogen atom or a cyano group,
R$_2$ signifies a hydrogen atom, a cyano, carboxylic acid ethylester or unsubstituted carboxylic acid amide or a methyl group,
R$_3$ signifies a hydrogen atom or a cyano, carboxylic acid ethylester or an unsubstituted carboxylic acid amide group,
R$_4$ signifies a hydrogen atom or a methyl radical,
A signifies the atoms required to form a condensed naphthalene, methoxynaphthalene or acenapthene ring or a condensed benzene ring which may be substituted by methyl and/or methoxy,
provided that if R$_1$ signifies the cyano group and R$_4$ signifies hydrogen, then either both substituents R$_2$ and R$_3$ are not hydrogen or one signifies hydrogen and the other signifies a cyano, carboxylic acid ethyl ester or carboxylic acid amide group and that if R$_1$ signifies hydrogen, at least one of the substituents R$_2$ and R$_3$ signifies a cyano or a carboxylic acid amide group.

The invention also provides a process for the production of compounds of formula I, which comprises
(a) cyclization of a compound of formula II,

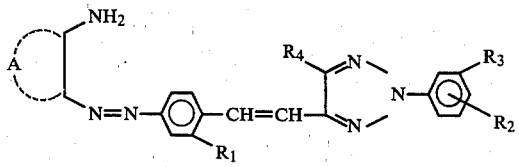

in which R$_1$ to R$_4$ and A are as defined above,
(b) cyclization of a compound of formula III,

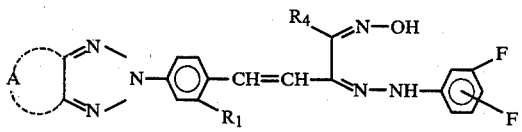

in which R$_1$ to R$_4$ and A are as defined above,
or
(c) condensation at 0° to 200° C., of a compound of formula IV,

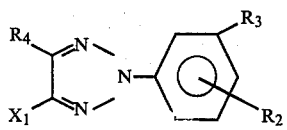

in which R$_2$, R$_3$ and R$_4$ are as defined above, with a compound of formula V,

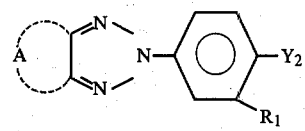

in which R$_1$ and A are as defined above,
and in which formula IV and V, one of the symbols X$_1$ and X$_2$ signifies a —CHO group or a functional derivative thereof such as the oxime, hydrazone or anile, and the other a —CH$_2$—Z group,
in which Z signifies hydrogen, cyano, carboxyl, an optionally substituted carboxylic acid amide or carboxylic acid ester group, or a

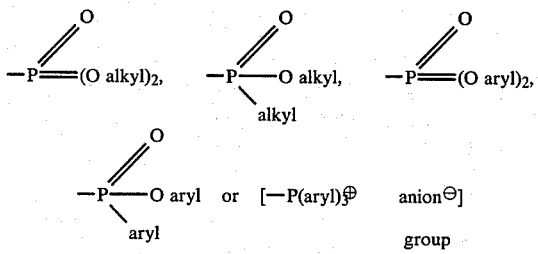

in which
alkyl is of 1 to 6 carbon atoms, and is optionally substituted, e.g. by methoxy, ethoxy, phenyl or phenoxy, and includes cycloalkyl, e.g. cyclohexyl,
aryl is optionally substituted phenyl and anion$^\ominus$ signifies a monovalent anion$^\ominus$ such as Cl$^\ominus$, Br$^\ominus$, I$^\ominus$, CH$_3$—O—SO$_3$$^\ominus$, C$_2$H$_5$—O—SO$_3$$^\ominus$, CH$_3$—SO$_3$$^\ominus$, C$_6$H$_5$—SO$_3$$^\ominus$ or ½ SO$_4$$^\ominus$.

In process variant (a), the oxidative cyclization of the ortho-aminoazo compounds of formula II is carried out in conventional manner and may be suitably carried out in the presence of an organic solvent stable to oxidation; examples of such are optionally halogenated or nitrated hydrocarbons such as benzene, toluene, chlorobenzene, ortho-dichlorobenzene, bromobenzene, nitrobenzene, 1,2-dichloroethane, 1,1,2,2-tetrachlorethane, amides such as dimethyl formamide, dimethyl acetamide, N-methyl pyrrolidone, phosphoric acid tris-(dimethylamide), sulphones such as tetramethylene sulphone, ethers such as methoxy and ethoxy benzene, dioxan, 1,2-dimethoxy and 1,2-diethoxyethane, tertiary amines such as dimethylamino and diethylamino-benzene, triethylamine, tri-(n-butyl)-amine, pyridine, picoline, quinoline and mixtures of pyridine bases. Suitable oxidizing agents are, for example, alkali hypohalogenites, e.g. sodium hypobromite, potassium hypobromite, lithium hypochlorite, chloride of lime, and preferably sodium hypochlorite, inorganic and organic copper (II) compounds such as copper (II) chloride, sulphate, acetate, carbonate or naphthenate, preferably in the presence of nitrogenous bases such as ammonia, amines such as trimethyl amine, methanolamine, diethanolamine, triethanolamine, pyridine, or air or oxygen in the presence of catalytic amounts of a copper (II) compound.

The reaction is conveniently carried out at temperatures from 0° to 50° C., e.g. from 0° and 80° C., preferably from room temperature to 80° C. in the case of the alkali hypohalogenites or from 20° to 130° C., preferably from 60° to 100° C., in the case of oxidation with a copper compound alone or with oxygen or air in the presence of a copper (II) compound.

If a diamine is used as coupling compound, it is preferable to remove the amino group remaining after triazole formation, e.g. by diazotization and subsequent boiling in the presence of a reducing agent such as hypophosphorous acid or one of its salts or an alcohol such as ethanol.

In process variant (b), the cyclization of compounds of formula III is carried out in conventional manner and may be effected for example, by simple condensation with cleavage of water or with the additional use of oxidizing conditions, under which a triazole-N-oxide compound is formed as intermediate and subsequently reduced to the corresponding triazole compound.

The simple cyclization of compounds of formula III can be carried out conveniently with the aid of dehydrating agents, e.g. anhydrides or halides, preferably chlorides, of organic carboxylic acids, such as acetic or propionic anhydride or chloride, or of phosphorus halides such as phosphorus trichloride, oxychloride or pentachloride, conveniently at temperatures of 0° to 150° C., preferably in the range of 20° to 130° C. Inert organic solvents can be used: hydrocarbons, halogenated hydrocarbons, ethers, amides such as phosphorus tris-(dimethyl amide), dimethyl formamide or acetamide, dimethyl sulphoxide, tetramethylene sulphonate, if acid halides are employed, or the reaction can be carried out in a great excess of acetic anhydride, optionally in the presence of one of the solvents named above, e.g. dimethyl formamide.

The oxidative ring closure can be accomplished by the action of various oxidizing agents. It is advisable to work with solvents stable to oxidation. In an acid, for example acetic acid, solution, bichromate or hydrogen peroxide are efficient oxidizing agents. In basic solvents such as pyridine or mixtures of pyridine and water, potassium ferricyanide, for example, is suitable. It is expedient to work at temperatures from room temperature to 150° C., preferably at 60° to 130° C.

The generally employable and therefore more preferred method consists in oxidation with copper (II) sulphate in pyridine-water at 90° to 100° C. It is not necessary to use stoichiometric amounts of copper, since the monovalent copper formed in the reaction can be continuously converted into the divalent form by blowing in air or oxygen. For the reduction of triazole-N-oxides to the triazoles the reaction can be carried out advantageously, for example, with base metals and acids such as zinc dust in acetic acid, in acetic acid-water mixtures or in mixtures of acetic acid and in an inert organic solvent such as chlorobenzene. It is suitable to work at room temperatures from about 150° C., preferably 60° to 130° C. If necessary the rate of reduction can be accelerated and/or reduction carried out at lower temperature by adding a small amount of an inorganic acid such as hydrochloric acid. The salts of the reducing acids of sulphur or phosphorus can also be used for reduction.

The reaction of a compound of formula IV with a compound of formula V in process variant (c), (Wittig synthesis or an analogous synthesis) is suitably carried out in the presence of a suitable catalyst or condensing agent, e.g. boric acid, zinc chloride, arylsulphonic acids, alkali or alkaline-earth salts of arylsulphonamides, acetic anhydride, alkali acetates, piperidine, alkali or alkaline-earth hydroxides, alkali or alkaline-earth alcoholates, at temperatures of 0° to 200° preferably at 20° to 160° C.

If the substituent Z in the reaction product is different from hydrogen, it is split off in a suitable manner, or more exactly replaced by a hydrogen atom. This can be effected by heating the compounds in which Z is a COOH group to temperature of about 200° C. in a solvent of high boiling point, e.g. a tertiary amine such as quinoline. If Z represents a cyano, carboxylic acid amide or carboxylic acid ester group, this is first saponified under acid or alkaline conditions to the carboxyl group. If Z represents an ester group containing phosphorus, such as

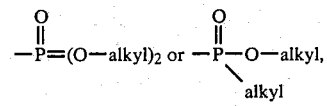

this group is replaced by a hydrogen atom during the reaction.

The reaction can be carried out by melting the reactants, but is carried out preferably in an inert solvent, e.g. in aliphatic or aromatic, preferably halogenated hydrocarbons, alcohols, ethers, glycols, amides such as formamide, dimethyl formamide or acetamide, N-methylpyrrolidone or phosphoric acid tris-(dimethylamide), acetonitrile, dimethyl sulphoxide and tetramethylene sulphone.

The compounds of formula V in which $X_2$ stands for $-CH_2-PO=(O\text{-alkyl})_2$ can be obtained from the corresponding compounds with a $-CH_2-Cl$ group by reaction with a trialkyl phosphite.

The compounds of formula I can be isolated by the normal methods, for example by filtration with suction if in suspension, by precipitation with a suitable precipitant and filtration with suction, by evaporation or steam distillation of the solvent and filtration with suction.

The preferred compounds of formula I correspond to the formula Ia,

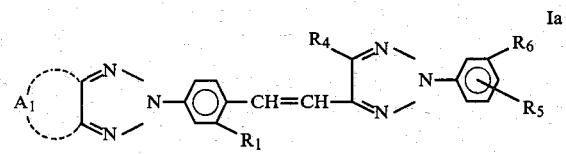

in which
R₁ and R₄ are as defined above,
R₅ signifies hydrogen, methyl or nitrile,
R₆ signifies hydrogen or nitrile,
A₁ signifies the atoms required for the formation of a condensed naphthalene, acenaphthene or benzene ring, the benzene ring being substituted by methyl and/or methoxy,
the provisos being as defined for formula I.

Particularly preferred compounds of formula Ia are those in which R₅ is in the para position to the triazoline ring, R₁ and/or one of the substituents R₅ and R₆ is nitrile and A₁ represents a condensed naphthalene ring.

The compounds of formulae II, III, IV and V are known or may be produced by known methods or in analogy with known methods from known starting materials.

The starting compounds of formula II can be produced, for example, by coupling a diazo derivative of an amine of formula VII,

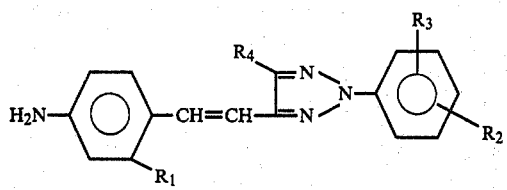

in which R₁ to R₄ are as defined above,
with compounds of formula VIII,

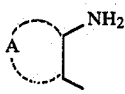  VIII in which A is as defined above and may bear a second primary amino group, at a pH in the range from 1 to 8, preferably 2 to 6, and at temperatures in the range of 0° to 60° C., i.e. initially at about 5° to 15° C. and for completion of coupling at about 50° to 60° C., in an aqueous or aqueous-organic medium, e.g. in a mixture of water and pyridine or a mixture of pyridine bases or in a urea solution.

The diazotization of the amines of formula VII, which are produced by the known methods or in analogy with the known methods, is carried out according to the known methods in aqueous solution or suspension or in aqueous-organic medium, e.g. in mixtures of water and glycols (ethylene glycol, propylene glycol, diethylene glycol), alcohol ethers (2-ethoxyethanol, 2-methoxyethanol, 2-n-butoxyethanol, 2-(2'-methoxyethoxy)-ethanol), ethers (dioxan, 1,2-dimethoxy-ethane), amides (dimethyl formamide, dimethyl acetamide, phosphoric acid tris-(dimethylamide), sulphones (etramethylene sulphone), using an alkaline or alkaline-earth nitrite and in the presence of a mineral acid at temperatures of −10° to +20° C., preferably at 0° to 10° C.

Suitable coupling components of formula VIII are, for example, 1-amino-3,4-dimethylbenzene, 1-amino-4-methyl-5-methoxybenzene, 1-amino-4,5-dimethoxybenzene, 1,3-diaminobenzene, 1,3-diamino-4-methylbenzene, 1,3-diamino-4-methoxybenzene, 2-aminonaphthalene-1-sulphonic acid, naphthyl-2-sulphonic acid, naphthyl-2-aminoethylsulphonic acid and diphenyl-4-aminomethylsulphonic acid or 4- or 5-aminoacenaphthene. The coupling components which contain one sulphonic acid group (which is split off in coupling) have the advantage in comparison with the corresponding compounds free from sulphonic acid groups that they are soluble in water in the form of the alkali-metal and ammonium salts and that they are physiologically less hazardous.

With the coupling components which bear one sulphonic acid group bound directly to the coupling position or to the amino group or through a —CH₂— group, the sulphonic acid or —CH₂—SO₃H group may be split off simultaneously with coupling or after the coupling reaction.

The compounds of formula III may be produced, for example, by reaction of oximinoketones of formula IX,

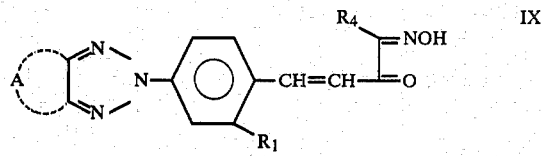

in which R₁, R₄ and A are as defined above,
with hydrazines of formula X,

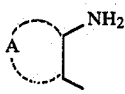  X in which R₂ and R₃ are as defined above.

The reaction can be conveniently be carried out, for example, in an inert organic, preferably polar solvent, e.g. in aliphatic or aromatic, preferably halogenated hydrocarbons, alcohols, ethers, glycols, amides such as formamide, dimethyl formamide or acetamide, phosphoric acid tris(dimethylamide), N-methylpyrrolidone, sulphoxides or sulphones such as dimethyl sulphoxide, tetramethylene sulphone, or acetonitrile or in a lower alkanecarboxylic acid such as acetic acid or propionic acid. It is preferred to work at temperatures of 0° to 100° C., more preferably in the range of 20° to 60° C., in the presence of an acid, preferably an organic lower carboxylic acid such as formic, acetic, propionic, butyric, oxalic, tartaric, lactic, citric acid etc.

In the production of compounds of formulae V and IX the formation of the triazole ring can be carried out analogously to the procedure described for the compounds of formula II, by diazotization of the corresponding amino compounds, coupling with a coupling component of formula VIII and oxidative ring closure. In the case of compounds of formula IX the oximinacetone grouping is subsequently formed or introduced.

The new triazolylstyrene compounds of formula I exhibit optical brightening properties and may be used for the optical brightening of a wide variety of organic polymeric materials. By "organic polymeric materials" are understood plastics materials and in particular fibres such as cotton and wool, but primarily synthetic fibre-forming high polymers such as polyesters, polyamides, polyurethanes, polyolefins (polyethylene, polypropylene), polyvinyl acetate, polyvinyl chloride, polyvinylidene chloride, polyacrylonitrile, modified polyacrylonitrile, polystyrene, cellulose diacetate and cellulose triacetate.

The triazolylstyrene compounds of formula I can be applied by the normal methods for optical brightening agents, for example in the forms of solutions in water or organic solvents or as aqueous dispersions. They can also be incorporated in spinning solutions and melts, in materials for injection moulding and in the monomers or prepolymers prior to synthesis of the final polymer.

The amounts used usually range from 0.001 to 0.5% preferably 0.01 to 0.2% by weight, and may vary depending on the method of application. A compound of formula I may be employed alone or in combination with an other brightener or compound of formula I and may be used in the presence of surface-active agents such as detergents, carriers and chemical bleaching agents.

For brightening polyester fibres in the form of fabric, it is especially advantageous to apply the compound of formula I to the fabric from an aqueous medium containing a surface-active agent by a padding process and to submit the fabric to dry heat treatment, preferably at 150°–240° C., according to the "thermosol" process.

The compounds give a neutral, red-violet to blue fluorescence shade, a very high saturation value and excellent light fastness.

In the following Examples the parts and percentages are by weight and the temperatures in degrees centigrade. The melting points are uncorrected.

EXAMPLE 1

20 Parts of 4-amino-2-cyano-β-[2'-(4''-cyanophenyloso)-triazolyl]-styrene are thoroughly mixed with 60 parts of dimethyl formamide, with cooling to 5°. Consecutively, 30 parts of 35% hydrochloric acid, 40 parts of water and 60 parts of ice are added. A solution of 5 parts of sodium nitrite in 20 parts of water is added for diazotization, the temperature being maintained at 0° to 5° during the reaction. After the reaction stirring is continued for 2 hours at 5°–8°, then the excess nitrous acid is decomposed with urea or sulphamic acid.

Meanwhile 9.5 parts of finely pulverised 2-aminonaphthalene are suspended in 40 parts of pyridine and 20 parts of 2/normal sodium hydroxide solution. This suspension is added in 10 minutes at 5°–10° to the strongly acid diazo suspension. The coupling mixture, which has a pH between 5 and 6, is held for 1 hour at 40°–50° with stirring and then cooled. The red azo compound settles out and is filtered with suction, washed with water until neutral, and dried.

21 Parts of the red azo compound, melting point 210°–213°, thus formed are mixed with 8 parts of crystallized copper acetate and 100 parts of pyridine. The mixture is reacted for 4 hours at 105° with stirring and the introduction of a powerful air stream. After cooling, the naphthotriasolyl compound formed is filtered, washed with ice-cooled methanol and then with water until the wash liquid is colourless, and dried. On recrysrallization from 500 parts of o-dichlorobenzene, 18 parts of acicular, lemon-coloured crystals, melting point 323°–325°, are obtained. The absorption maximum of the compound is at 377 nm and its structural formula is Ib,

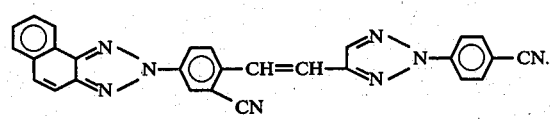

Ib

The fluorescence emission in polyester is 430 nm.

The 4-amino-2-cyano-β-[2'-(4''-cyanophenyloso)-triazolyl]-styrene used as starting compound can be obtained in conventional manner by condensation of 2-(p-cyanophenyl)-4-formyltriazole with 4-nitro-2-cyanotoluene in the presence of piperidine and pyridine, with subsequent reduction of the nitro group by the Béchamp method.

EXAMPLE 2

4.2 Parts of the compound of formula XII,

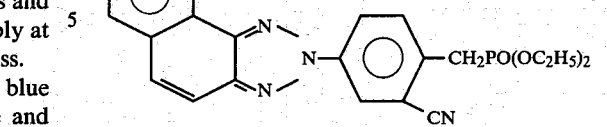

XII are dissolved with 2 parts of 2(p-cyaophenyl)-4-formyltriazole in 16 parts of anhydrous dimethyl formamide. 4.4 Parts of a methanolic sodium methylate solution containing 1.2 parts of sodium methylate are added. The reaction mixture is heated for 1 hour at 60° and then cooled to 10°, and 20 parts of ice-cold methanol are added. The pale yellow precipitate is filtered off with suction and worked up as described in Example 1. 3.4 Parts of pale yellow crystals, melting point 323°–325°, are obtained which correspond to the compound of formula Ib.

The phosphonate of formula XII can be produced as follows: 21 Parts of 2-cyano-4-naphthotriazole-2-yl toluene are mixed with 13.1 parts of N-bromosuccinimide, 0.2 parts of benzoyl peroxide and 700 parts of carbon tetrachloride dried over phosphorous pentoxide. The mixture is reacted for 7 hours with reflux. After cooling, the succinimide formed is separated by filtration and the filtrate evaporated in a Rotavapor. A white powder with melting point 161°–164° is obtained, which without further purification is added to 80 parts of triethyl phosphite and heated with reflux until no further ethyl bromide is generated. The excess triethyl phosphite is distilled together with the ethyl bromide. The residue consists of the virtually pure phosphonate of formula XII.

EXAMPLE 3

If Example 2 is carried out using 1.9 parts of 2-phenyl-4-formyl-5-methyltriazole in place of 2 parts of 2-(p-cyanophenyl)-4-formyltriazole, 4 parts of lemon crystals, melting point 232°–233°, are obtained. In chloroform the compound absorbs at 375–378 nm and in chlorobenzene solution it fluoresces with violet shade ($F_{em}$ 435 nm). It has the formula Ic,

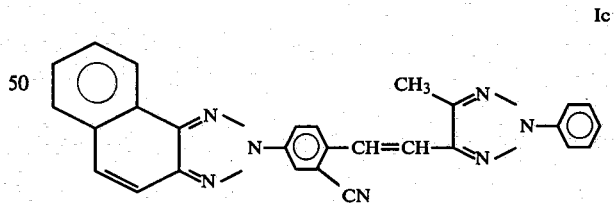

Ic

This compound is suitable for application in polyester melts for brightening the spun fibre, and it has high light fastness.

EXAMPLE 4

10 Parts of 4-amino-β-[2'-4''-cyanophenyloso)-triazolyl]-styrene are mixed with 30 parts of 2-methoxyethanol and 11 parts of dimethyl formamide with cooling to 5°, then 15 parts of 35% hydrochloric acid, 40 parts of water, 30 parts of ice and a solution of 3 parts of sodium nitrite in 10 parts of water are added consecutively. The suspension is stirred at 5° until diazotization is complete, then the small excess of nitrous acid is decomposed with urea. A solution of 5 parts of 2-aminonaphthalene in 50 parts of pyridine is added to the well stirred suspension of the diazonium salt. The product is 15 parts of a red-brown compound, melting point in the crude state 150°–160°. The compound is suspended in 50 parts of pyridine along with 7.5 parts of crystallized copper acetate, the suspension raised to 105° and held at this temperature for 2 hours with the introduction of a powerful air stream. 10 Parts of a yellow naphthotriazole compound are obtained, which after recrystallization from 600 parts of chlorobenzene melts at 292°–294°. This compound has the formula Id, and 2 parts of 2-(p-cyanophenyl)-4-formyltriazole are dissolved in 20 parts of anhydrous dimethyl formamide. 4.4 Parts of a solution of 1.2 parts of sodium methylate in methanol are added dropwise. The suspension is held for 2 hours at 50°, cooled to 10° and set with 25 parts of ice-cold methanol. The product is filtered and worked up as described in Example 4. 3.4 Parts of yellow crystals melting point 292°–294°, are obtained, which correspond to the compound of formula Id.

The phosphonate of formula XVI is obtained as follows: 2.9 Parts of 4-naphthotriazole-2-yl toluene, 9.8 parts of N-bromosuccinimide (10% excess) and 0.1 part of benzoyl peroxide are added to 120 parts of carbon

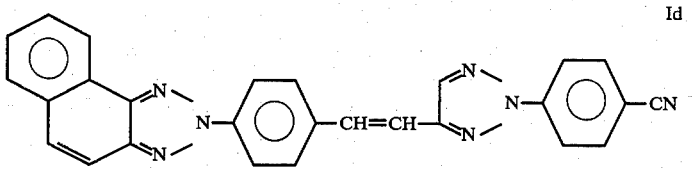

Id

Its absorption maximum in chloroform is at 370 nm and in chlorobenzene solution it exhibits pronounced redviolet fluorescence ($F_{em}$ 427 nm).

If the 10 parts of 4-amino-β-[2'-(4''-cyanophenyloso)-triazolyl)-styrene in this Example are replaced by the equivalent amount of 4-amino-β-[2'-(3''-cyano-4''-methylphenyloso)-triazolyl]-styrene, the optical brightener of formula Ie, tetrachloride dried over phosphorus pentoxide. The solution is reacted for 6 hours with reflux. The succinimide formed is filtered hot, then the filtrate is evaporated in a Rotavapor. 19.7 Parts of white crystals with melting point 237°–241° are obtained. The crystals are added to 150 parts of triethyl phosphate and the solution held at the boil until formation of ethyl bromide is complete. After distillation of the excess triethyl phosphize

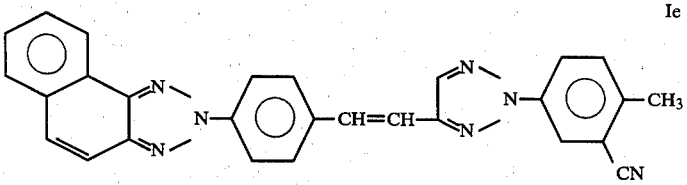

Ie is obtained in the form of pale yellow crystals with melting point 245°–247°, an absorption maximum at 370 nm and a violet fluorescence shade in chlorobenzene.

EXAMPLE 5

3.95 Parts of the phosphonate of formula XVI,

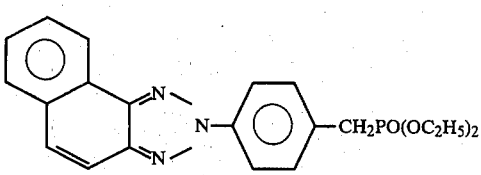

XVI in vacuum, the phosphonate of formula XVI is obtained in oily, poorly crystallizing form and is employed further at once in this form.

The following table specifies further triazolylstyrene compounds of formula If,

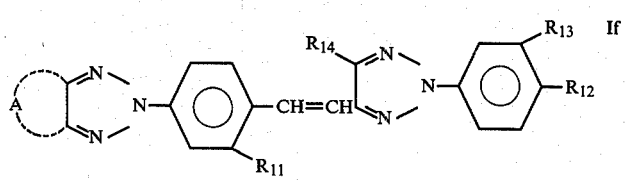

If which are producable according to the procedures of Examples 1 to 5 and are distinguished by the significance of the substituents and the fluorescence shade in chlorobenezene.

Table

| Example | A | $R_{11}$ | $R_{12}$ | $R_{13}$ | $R_{14}$ | Fluorescence shade |
|---|---|---|---|---|---|---|
| 6 | naphthalene with CH$_3$O substituent | H | CN | H | H | blue-violet |
| 7 | CH$_3$–, CH$_2$–O– substituted ring | H | CN | H | H | " |
| 8 | " | H | CH$_3$ | CN | H | violet |
| 9 | naphthalene with –CH$_2$–CH$_2$– bridge | H | CN | H | H | " |
| 10 | naphthalene | H | CONH$_2$ | H | H | " |
| 11 | " | H | CH$_3$ | CONH$_2$ | H | red-violet |
| 12 | " | CN | CONH$_2$ | H | H | blue |
| 13 | " | CN | CH$_3$ | CONH$_2$ | H | violet |
| 14 | " | H | CN | H | CH$_3$ | " |

Application Example A

10 Parts of the compound of formula Id are mixed with 22 parts of a highly sulphonated castor oil, 8 parts of sodium dioctyl phenyl polyglycol etheroxyacetate containing 40 ethenoxy groups in the molecule, and 80 parts of water. The mixture is ground in a suitable machine such as a sand mill until the particle size of the main fraction is 0.5 to 2 microns.

100 Parts of fabric of polyester (polyethylene terephthalate) fibre are entered into a bath at 50° prepared with 3000 parts of water, 15 parts of a carrier based on ortho-phenyl phenol and 2 parts of the dispersion formed as described above. The bath is raised to the boil in 30 minutes and held at the boil for 45 minutes, after which time the fabric is removed. It is then treated in a fresh bath containing 1.5 g/l octyl phenyl decaglycol ether for 10 minutes at 70° and 40:1 liquor ratio. On removal from this bath it is rinsed with warm water and dried. An intense optical white effect is obtained on the fabric. If the optical brightener is applied in enclosed equipment at 120°–130°, comparable white effects are obtained without the addition of a carrier.

Application Example B

Polyamide 6 (poly-α-caprolactum) granules are powdered in a mixer with 0.01–0.05% of their weight of the compound of formula Ib. The granules are conveyed into a melt spinning machine, where they are melted for 30 minutes at about 300° under nitrogen and the melt stirred for 15 minutes at this temperature. The melt is then brought up to the spinning temperature, 285°, and spun as monofilament at 3–5 excess atmospheres pressure (nitrogen). The filaments show violet fluorescence in daylight. They appear much whiter and brighter than comparable filament containing no optical brightener.

If polyester or polypropylene is used in place of polyamide and the melt spun at 290° or 260° respectively, filaments showing a higher degree of whiteness are obtained compared with the unbrightened substrate.

Application Example C

In the tank of a melt spinning machine 200 parts of polyethylene terephthalate are melted at 280° in a nitrogen atmosphere and 0.04 parts of the compound of formula Ie are added to the melt. The optical brightening agent melts at this temperature and is stirred with the polyester until homogeneously distributed, after which 4 parts of titanium dioxide are added as delustrant, with continued stirring a nozzle, the filament chilled by a water jet, cold drawn and reeled on bobbins.

Products made of this filament have an appreciably whiter appearance than products of filament produced by the same process but without the addition of the optical brightening agent.

If one of the compounds of formula Ib, Ic or Id is used in place of that of formula Ie, similar white effects are obtained.

Application Example D

A fabric of polyester (polyethylene terephthalate) fibre is padded at room temperature with an aqueous dispersion containing per liter 0.1 to 0.6 parts of the compound of formula Id and 1 part of the adduct of about 8 mols of ethylene oxide on 1 mol of p-tert. octyl phenol. The expression on the padding machines leaves the fabric retaining 80% of its weight of liquor. It is dried for 30 minutes at 60° and heated in dry heat at 180° to 220° for a few seconds to one minute depending on the temperature. The treated fabric has a considerably whiter appearance than untreated material.

If a blend fabric, e.g. of polyester fibre and cotton, is used in this Example in place of a 100% polyester fabric, the optical brightening effect is similar to that obtained on the latter fabric.

Application Example E

100 Parts of moulding material consisting of 65 parts of polyvinyl chloride, 35 parts of a phthalate dioctyl as plasticizer, and 2%, in relation to the polymer, of a stabilizer are mixed with 0.005 parts of the compound of formula Ib dissolved in the plasticizer. The material is worked on a roller mill for 10 minutes at 150°–160° and extruded as film. If opaque film as desired, 2.5% titanium dioxide is admixed with the material before processing. The films are of superior appearance to films of the same composition without an incorporated brightener.

What we claim is:

1. The compound of formula Ib,

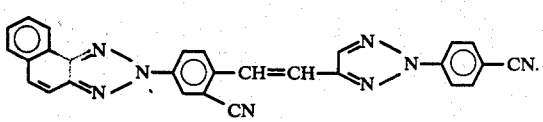

* * * * *